(12) United States Patent
Raupp

(10) Patent No.: US 7,073,877 B2
(45) Date of Patent: *Jul. 11, 2006

(54) CONTAINER INSPECTION MACHINE

(75) Inventor: Henry F. Raupp, Freeville, NY (US)

(73) Assignee: Emhart Glass S.A., Cham (CH)

( * ) Notice: Subject to any disclaimer, the term of this patent is extended or adjusted under 35 U.S.C. 154(b) by 267 days.

This patent is subject to a terminal disclaimer.

(21) Appl. No.: 10/610,060

(22) Filed: Jun. 30, 2003

(65) Prior Publication Data

US 2004/0262508 A1    Dec. 30, 2004

(51) Int. Cl.
*A47B 96/00* (2006.01)
(52) U.S. Cl. .................. 312/322; 250/223 B; 312/326; 312/329
(58) Field of Classification Search ............ 250/223 B, 250/223 R; 356/240.1, 426–428, 239.4–239.6; 312/239.1–239.7, 322, 326, 329
See application file for complete search history.

(56) References Cited

U.S. PATENT DOCUMENTS

| | | | |
|---|---|---|---|
| 2,051,946 A | 8/1936 | Hewlett | |
| 3,434,594 A | 3/1969 | Husome | |
| 3,886,356 A | 5/1975 | Gomm et al. | |
| 5,714,998 A | 2/1998 | Wheeler | |
| 6,226,081 B1 | 5/2001 | Fantone et al. | |
| 6,371,580 B1 * | 4/2002 | Claypool et al. | ........... 312/120 |
| 6,810,562 B1 * | 11/2004 | Horne et al. | ............. 312/249.7 |

OTHER PUBLICATIONS

Glass Magazine dated Jun. 2003, p. 150.

* cited by examiner

*Primary Examiner*—Stephone B. Allen
*Assistant Examiner*—Davienne Monbleau
(74) *Attorney, Agent, or Firm*—Spencer T. Smith

(57) ABSTRACT

A machine for inspecting a container which is being conveyed along a linear path. The machine has cabinets situated in front of the conveyor path at either side of a central open area in front of the conveyor path which is to be used by an operator for servicing the conveyor. The interior sides of these cabinets are open for access to electronics and the central opening is closed by a pair of doors which are releasably attached to the sides of the cabinets and can be push in to provide access to the central area and can be pulled from the cabinets to provide access to electronics through the open sides of the cabinets.

1 Claim, 6 Drawing Sheets

CONTAINER INSPECTION MACHINE

The present invention relates to machines which inspect bottles for defects and more particularly to such machines wherein a bottle is conveyed through one or more inspection stations via a linear conveyor system.

BACKGROUND OF THE INVENTION

Machines for inspecting glass bottles and the like are performing more and more inspections using camera technology. In such applications mirrors redirect images to a camera and massive light sources assure proper illumination. Access to this equipment is a high priority in the design of the machine since the environment within a factory making glass bottles is not clean requiring periodic cleaning of the light sources, mirrors and camera lenses.

OBJECT OF THE INVENTION

It is an object of the present invention to provide a machine for inspecting glass containers which will make required cleaning of the mirror's, etc. easier.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
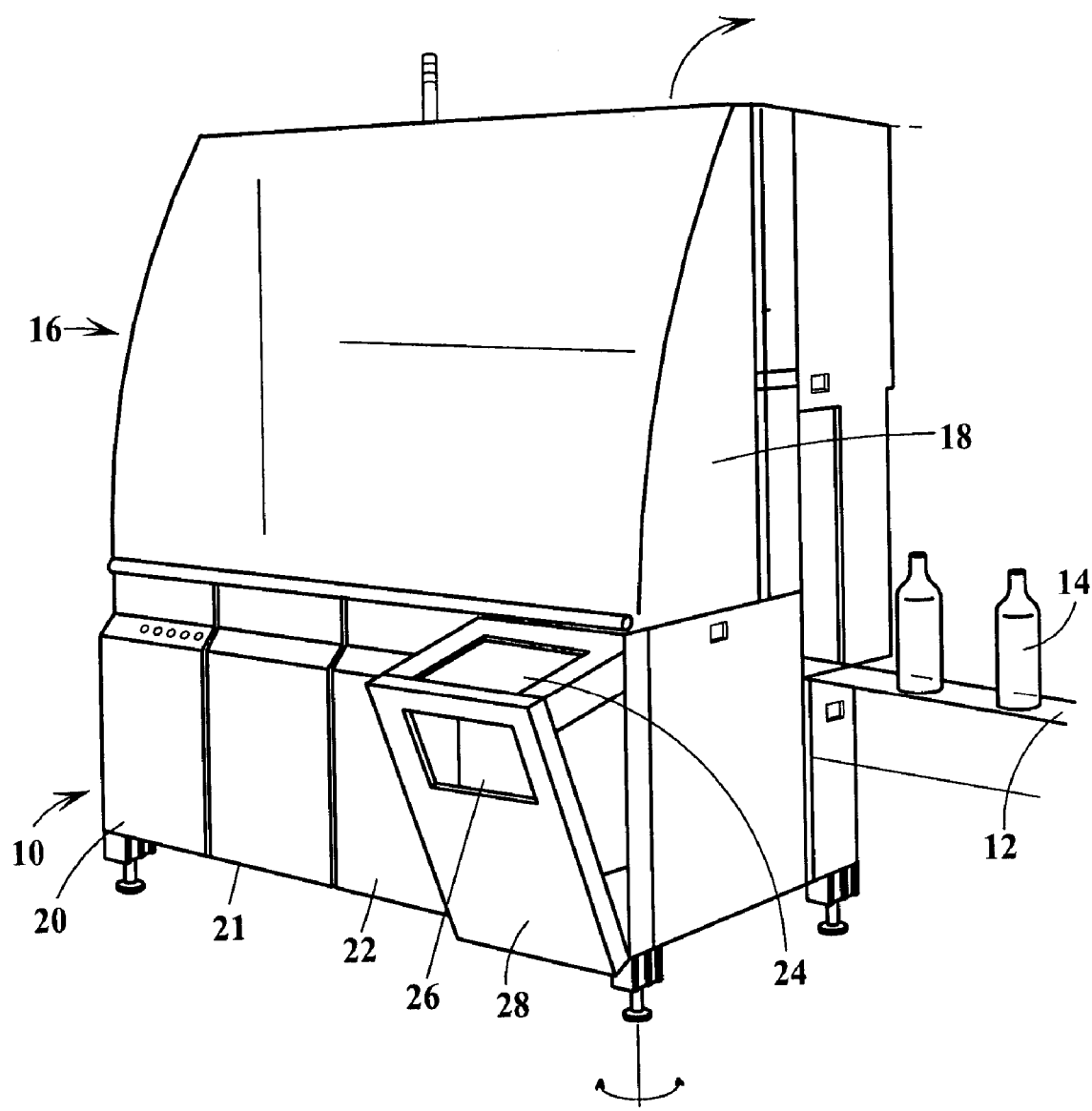
FIG. 1 is a schematic oblique view of an inspection machine for inspecting bottles made in accordance with the teachings of the present invention.

FIG. 1 shows a glass bottle inspection machine 10 which has a conveyor 12 for conveying bottles 14 through the machine. As the bottles proceed through the machine they will pass through any number of inspection stations. A plastic front closure 16 is pivotally mounted across the top so that it can be raised to provide access to the machine. This front closure 16 cooperates with two fixed side panels 18 to close the machine.

Below the closure are three front panels 20,21,22 and a console 24 that can be used by an operator to operate the machine. When not in use the console can be pushed down against the front wall of the cabinet and will be covered by the window 26 in the front wall cover 28 which pivots to a vertical position (see U.S. Pat. No. 6,371,580). This structure is secured to the frame via a vertical pivot (not shown) at the right side so that it can pivot outwardly providing frontal access to the electronics stored within. The left most panel 20 can be released via a screw 30 (FIG. 2) and removed from the frame to provide frontal access to the electronics stored within.

Figure 2:
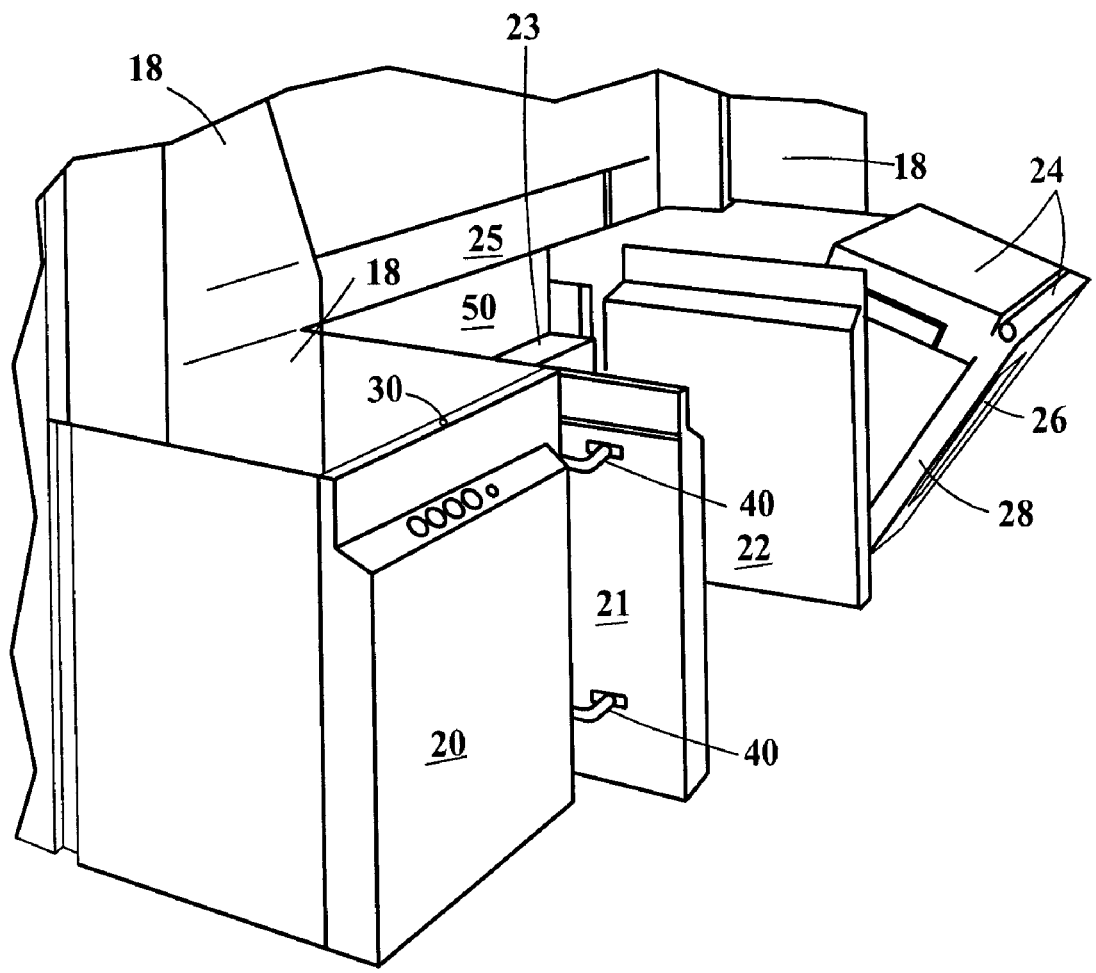
FIG. 2 is an oblique view of a portion of the machine with the top cover raised and the center doors pushed open.
Figure 3:
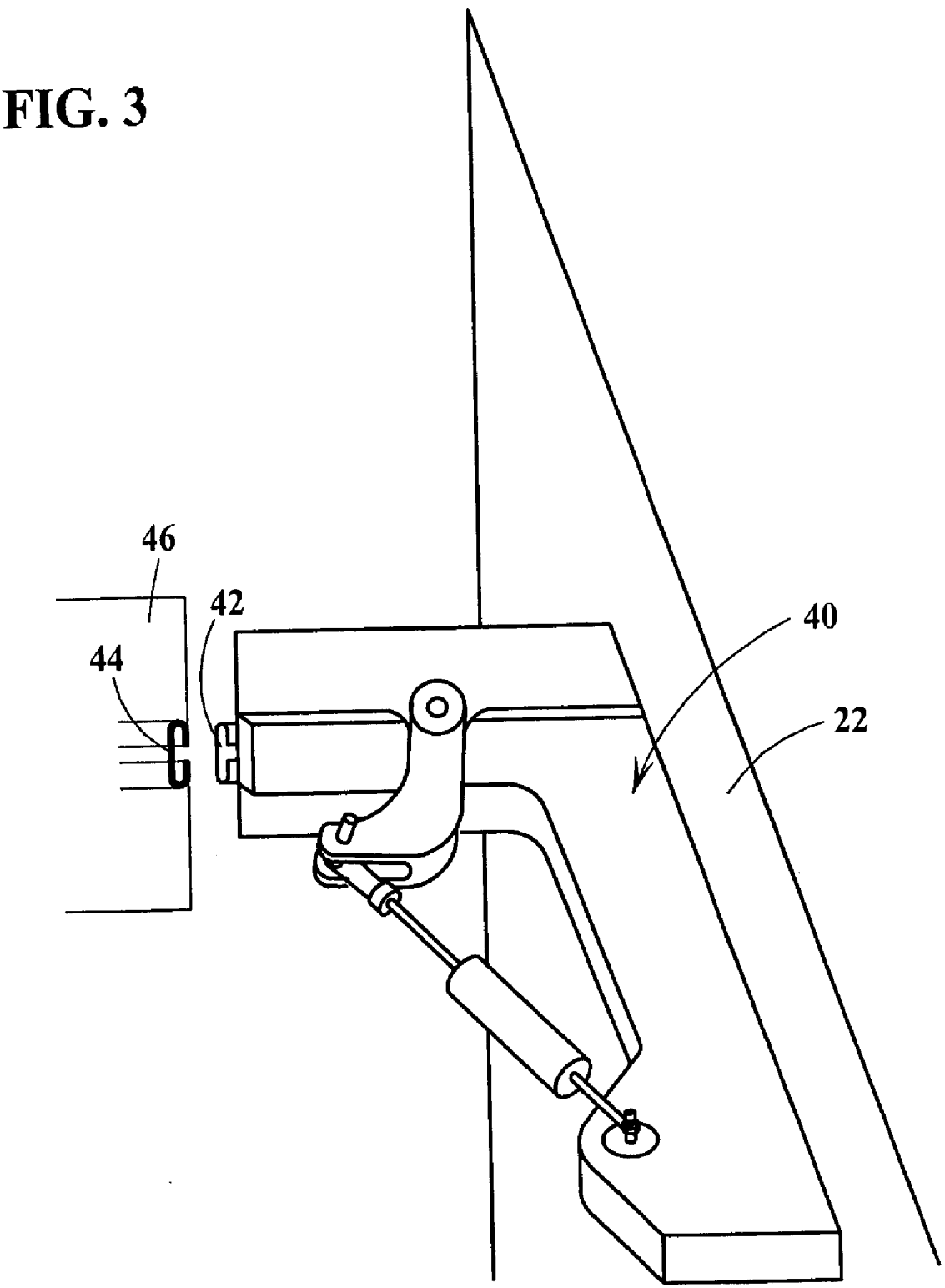
FIG. 3 is an oblique view of a door hinge shown in FIG. 2.
Figure 4:
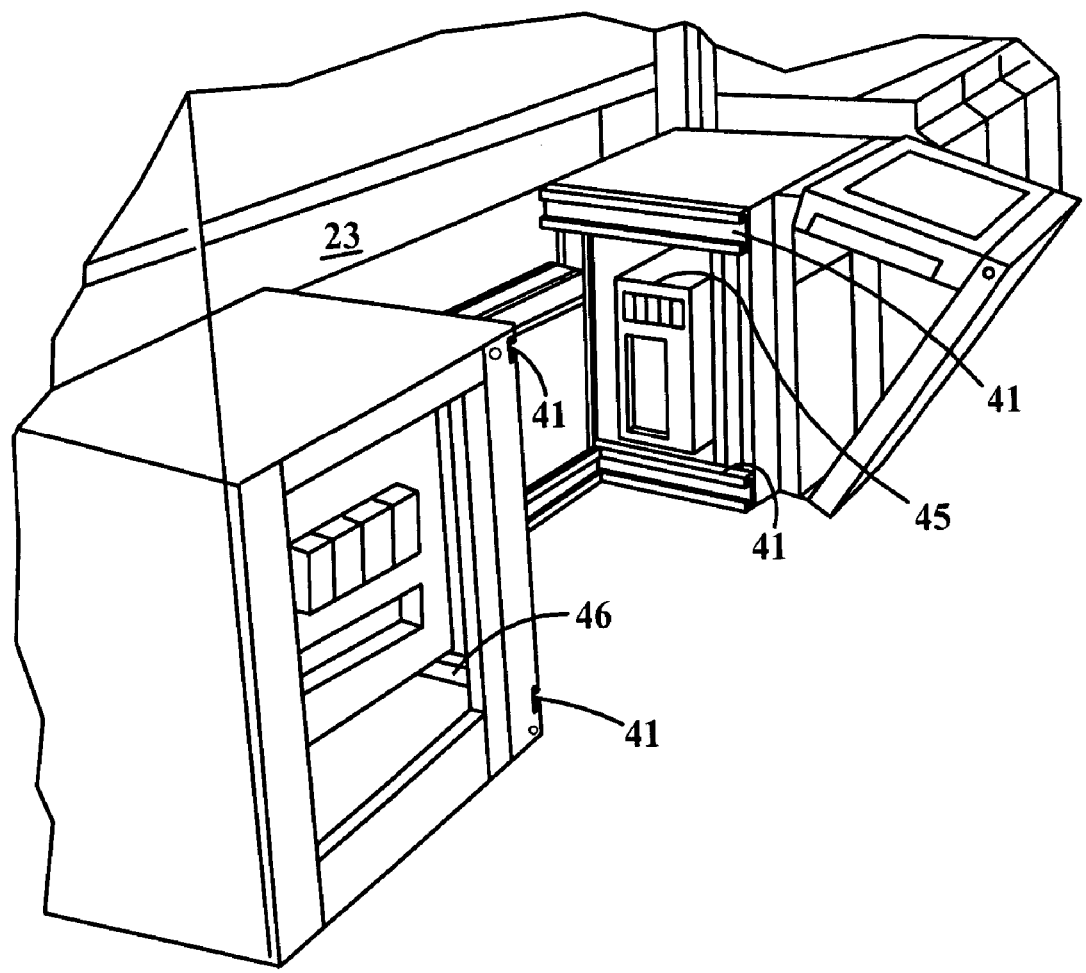
FIG. 4 is a view similar to that of FIG. 2 with all the doors and panels removed.

FIG. 2 shows that the pair of center panels 21, 22 are doors which open inwardly into an open chamber 23 into which an operator can enter for working in close proximity with the conveyor path 25. As shown each door has upper and lower hinges 40 which are secured to an elongated key member 42 (FIG. 3) which slides into an elongated horizontal keyway 41 which is part of the machine framework 46.

As can be seen from FIG. 2, since the keyway extends to the front of the machine, each door can be completely removed from the machine by pulling the key 42 out of the keyway 41. With the doors removed the side opening 45 in the right hand cabinet and the side opening 46 in the left hand cabinet will be exposed thereby providing access from the side to the cabinets.

Finally, also exposed when the doors are opened is a panel 50 (FIG. 2) covering the storage area beneath the conveyor path 25. This panel operates like the front left panel to provide access to the electronics stored behind this panel.

Figure 5:
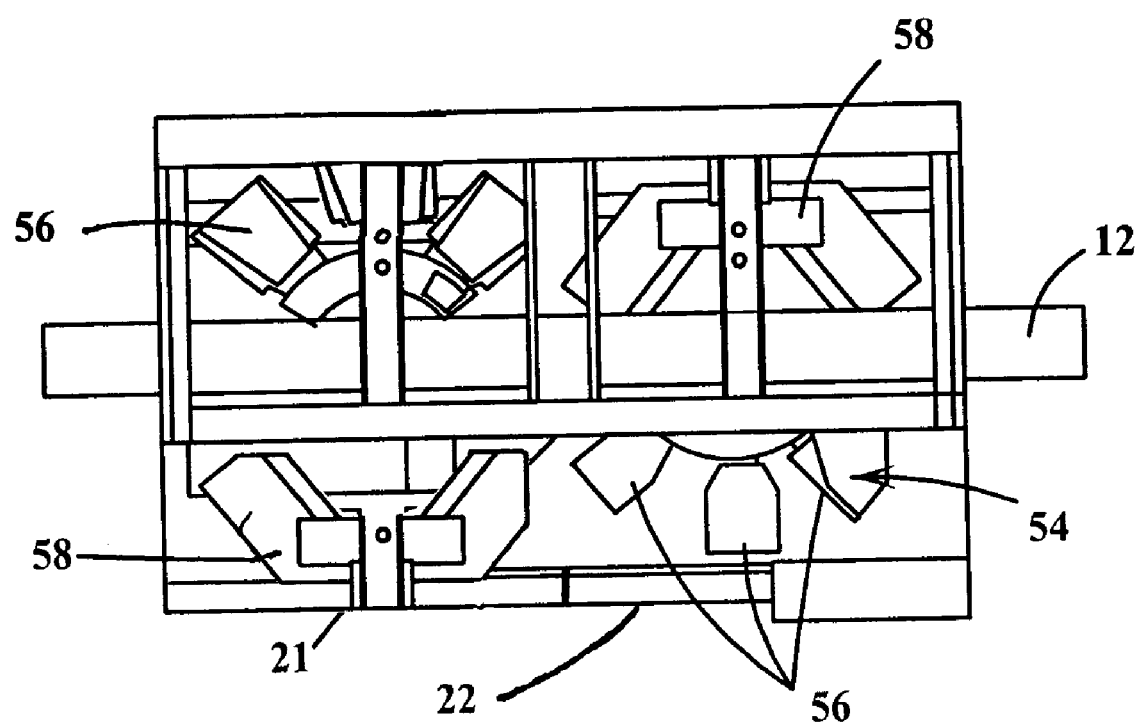
FIG. 5 is a top view of the machine having an alternate embodiment, in the operating mode, with the top cover removed.
Figure 6:
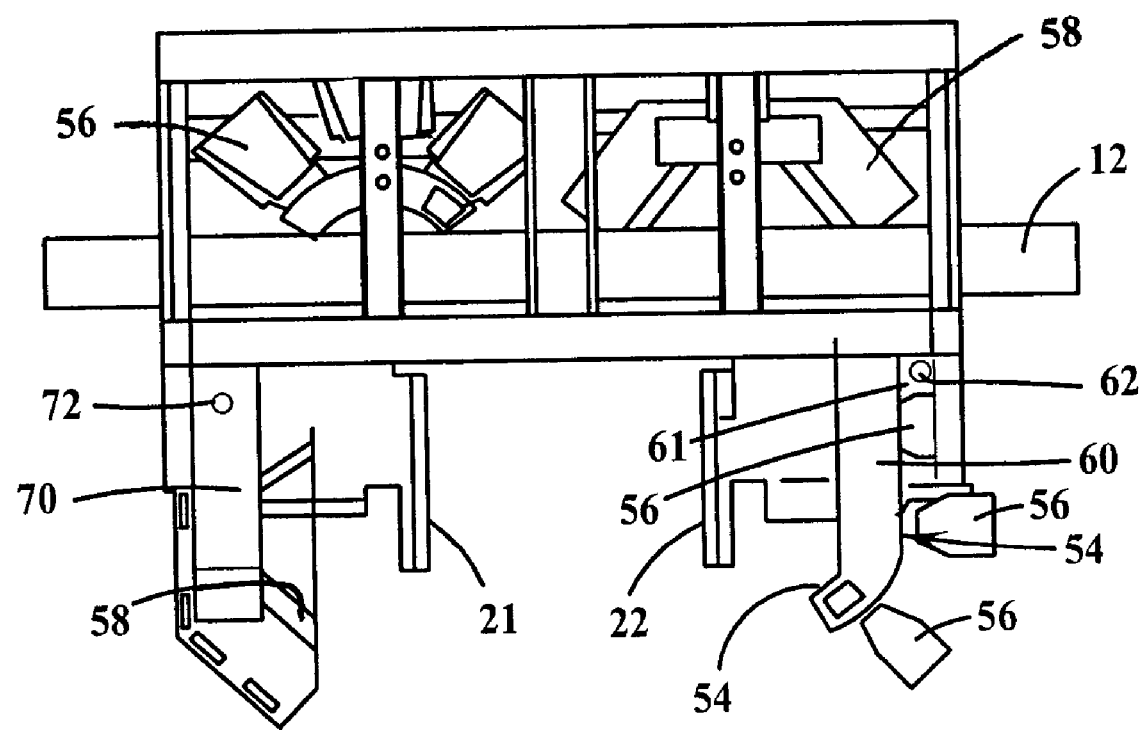
FIG. 6 is a top view of the machine having the alternate embodiment, in the servicing mode.

In a second embodiment shown in FIGS. 5 and 6 (the front cover has been removed for clarity), the bottles pass through right hand and left hand inspection stations. The right hand station is defined by a right hand mirror assembly 54 which supports three mirrors 56, a light source assembly 58 in the form of a large array of L.E.D.'s which is rigidly mounted on the machine frame 46 and a camera system (not shown) also mounted on the machine frame. The left hand station is defined by a mirror assembly 54 which supports three mirrors 56 and which is rigidly mounted on the machine frame, a light source assembly 58 in the form of a large array of L.E.D.'s and a camera system (not shown) also mounted on the machine frame.

As can be seen from FIG. 6, the right hand mirror assembly 54 is mounted on a horizontal arm 60 which is secured at its end proximate the conveyor path, to a vertical column 61 which is mounted on a pivot shaft 62 located at the right end of the machine. The right hand mirror assembly can therefore be pivotally displaced between a retracted service position shown in FIG. 6 and the operating position shown in FIG. 5. The left end light source assembly 58 is mounted on a horizontal arm 70 which is secured at the interior end to a pivot shaft 72 located at the left end of the machine. The left hand light assembly can therefore be pivotally displaced between a retracted service position shown in FIG. 6 and the operating position shown in FIG. 5 where it will be clear of the open area so that a serviceman can service the conveyor path and the equipment at the first and second stations.

When the machine is in the servicing mode with the left-hand light source assembly and the right hand mirror assembly are at their service position and the front doors 21,22 open, an operator can step into the chamber 23 and conveniently address any issues involving bottles being conveyed along the conveyor or service all of the mirror and light source assemblies.

The invention claimed is:

1. A machine for inspecting a container which is being conveyed along a linear path comprising
    first cabinet means in front of and at the left end of the linear path,
    second cabinet means in front of and at the right end of the linear path defining an open area in front of the linear path and between the first and second cabinet means, said first and second cabinet means having open sides defining the sides of the open area, first and second doors, first mounting means for mounting said first door on the open side of said first cabinet means so that said first door can be pushed from a closed position closing entry into the open area to an open position against said open side and so that said first door can be removed from said first cabinet means to provide access to the open side of said first cabinet means, second mounting means for mounting said second door on the open side of said second cabinet means so that said second door can be pushed from a closed position closing entry into the open area to an open position against said open side of the second cabinet means and so that said second door can be removed from said second cabinet means to provide access to the open side of said second cabinet means.

* * * * *